United States Patent [19]

Gundlach et al.

[11] Patent Number: 4,796,688

[45] Date of Patent: Jan. 10, 1989

[54] METHOD FOR CONTROLLING THE MELTING AND CASTING PROCESS IN PRECISION CASTING, PARTICULARLY FOR DENTAL ENGINEERING, AND ARRANGEMENT FOR CARRYING OUT THE METHOD

[75] Inventors: Hans-Werner Gundlach, Bremen; Friedrich Jacob, Lilienthal, both of Fed. Rep. of Germany

[73] Assignee: Bego Bremer Goldschagerei Wilh. Herbst GmbH & Co., Bremen, Fed. Rep. of Germany

[21] Appl. No.: 94,056

[22] Filed: Sep. 4, 1987

Related U.S. Application Data

[63] Continuation of Ser. No. 826,399, Feb. 5, 1986, abandoned.

[30] Foreign Application Priority Data

Feb. 15, 1985 [DE] Fed. Rep. of Germany ....... 3505346

[51] Int. Cl.$^4$ ............................................. B22D 37/00
[52] U.S. Cl. ..................................... 164/457; 164/155
[58] Field of Search ................ 164/4.1, 150, 154, 155, 164/457

[56] References Cited

U.S. PATENT DOCUMENTS 3,620,294 11/1971 Hetzel et al. ....................... 164/155
3,788,382 1/1974 Daniel et al. ....................... 164/155

FOREIGN PATENT DOCUMENTS 2638595 3/1978 Fed. Rep. of Germany .
2849598 6/1979 Fed. Rep. of Germany ....... 164/4.1
3146391 5/1983 Fed. Rep. of Germany .
3315835 11/1984 Fed. Rep. of Germany .

Primary Examiner—M. Jordan
Assistant Examiner—Richard K. Seidel
Attorney, Agent, or Firm—Sughrue, Mion, Zinn, Macpeak & Seas

[57] ABSTRACT

The variation with time of the temperature is analyzed during the heating-up of a melting charge in dental engineering. If the slope ($d\theta/dt$) of the temperature curve changes by a predetermined measure, this is used for detecting the liquidus point. Time and/or temperature for casting the melt are determined by a criterion ($\Delta\theta$; $\Delta t$) referring to the liquidus point determined in this manner. The values determined for the casting time and other casting parameters are stored and used as controlling variables for subsequent melting and casting processes. In addition, the entire temperature variations of successive processes can be stored. A subsequently measured temperature variation is compared with the stored temperature variations during the measurement (section by section). In the case of agreement (within predetermined tolerances) an identified stored temperature variation is used as nominal variation for the further melting and casting process.

14 Claims, 10 Drawing Sheets

METHOD FOR CONTROLLING THE MELTING AND CASTING PROCESS IN PRECISION CASTING, PARTICULARLY FOR DENTAL ENGINEERING, AND ARRANGEMENT FOR CARRYING OUT THE METHOD

This is a continuation of application Ser. No. 826,399, filed Feb. 5, 1986, now abandoned.

DESCRIPTION OF THE INVENTION

The invention relates to a method for controlling the melting and casting process in precision casting, particularly for dental engineering, and to a device for carrying out the method.

Semi-automatic or fully automatic control devices for the melting and casting process are known from the following printed documents: German Offenlegungsschrift No. 2,158,115, German Auslegeschrift No. 2,638,559, German Offenlegungsschrift No. 2,856,304, German Offenlegungsschrift No. 3,146,391, German Offenlegungsschrift No. 3,305,418, German Offenlegungsschrift No. 3,315,835, U.S. Patent Specification No. 3,620,294 and the pamphlet "PRESTOMAT B1" by the firm of DEGUSSA. In addition, a Similar control system is known from German Offenlegungsschrift No. 3,345,542 published after the date of priority of the present application.

The disadvantageous feature of these known methods or devices is that the casting temperature of the melting charge must be known as accurately as possible and that measuring errors due to aged measuring sensors, different radiation properties of the crucibles and so forth can falsify the entire casting result to such an extent that the melt or the casting are unusable. This is because, if the casting temperature is selected too low, the melting charge is not yet completely molten, that is to say primary crystals are still present which leads to unsatisfactory casting results. If, conversely, the casting temperature is set too high, porous spots occur in the moulded part during casting.

Another problem lies in the fact that the optimum casting temperature has different values for various alloys, which hitherto had to be determined empirically. For this purpose, it was necessary to know the exact composition of the alloy or to carry out elaborate tests for determining the optimum casting temperature before the actual casting.

For this reason, the invention has the objective of improving method and device of the generic type to the point where the optimum casting temperature and the optimum casting time can be determined in a simple manner.

This objective is achieved by the features specified in the characterising clause of the claims.

In the invention, the finding is utilized that the variation with time of the temperature or of the radiation intensity of the melting charge and, particularly, the variation with time of the temperature (differential quotient or difference quotient) provide excellent information on the state of the melting charge. Particular attention is paid to the melting interval. In the case of alloys, a distinction is made between solidus temperature and liquidus temperature. During the heating-up, the first melting occurs at the solidus temperature. At that point, the melt still contains primary crystals which are completely molten only when the liquidus temperature is reached. The melt is then liquid. When the liquidus temperature is reached in the crucible, the melt collapses to a spherical shape and thus has the smallest possible surface when the liquidus temperature is reached. This reduction in surface also explains the effect in German Auslegeschrift No. 2,638,559 that the induced power is suddenly reduced at the liquidus point when an induction furnace is used.

During the initial heating-up, the temperature of the melt continuously rises up to the solidus temperature. The heat supplied is then needed for phase conversion. During the phase conversion, the temperature of the melt rises with a different gradient. In some alloys, it almost does not rise at all whereas in other alloys the flattening of the temperature curve is only very indistinct. After complete phase conversion (liquidus temperature) the temperature rises again with a steeper gradient if further power is supplied.

It is one aspect of the invention that the melting interval is automatically identified by evaluating the variation with time of the temperature and that the melting interval is extended by external control of the heating power. The latter feature is of significance particularly in the case of alloys in which the temperature curve has only a faintly defined flattening in the melting interval. This also counteracts the effect that the melt is only inhomogeneously heated with the normally high heating power of an induction coil and thus, for example, the liquidus temperature is already reached at the surface whereas no complete phase conversion has yet taken place in the interior of the melt. This can be explained by the fact that the magnetic field creates induction currents in the heated melt which increase the temperature and that with high power or high frequencies, the outer layers of the melting charge are heated to a greater extent than the interior of the melt due to the "skin effect". In this case, the melting interval is not distinctly defined and, in particular, there is no clearly recognisable horizontal section in the temperature curve. For this reason, and in order to achieve a homogeneous temperature in the melt, according to one aspect of the invention, the heating power is switched back when the solidus temperature is approached or at the latest when this temperature is reached, whereas it is switched to higher values again during the heating-up to the solidus temperature and after the melting interval has been reached. According to an aspect of the invention, after the melting interval has been passed, the melting charge is further heated up by a predetermined temperature value until the casting temperature is reached.

This temperature value, by which the melt is overheated after the liquidus temperature has been reached, could be externally preset by the operator (for example 100° C. above the liquidus temperature). But this entails the risk of operating errors, especially since the respectively optimum value of the excess temperature increase (past the liquidus temperature) also depends on other factors such as, for example, the type of alloy used, the quantity to be cast and so forth.

For these reasons, the most important aspect of the invention deals with the problem of determining the optimum casting temperature and the optimum casting time on the basis of the liquidus point. For this purpose, the invention proposes several variants. In a first variant, heating is continued for a preset period of time (for example 22 s) after the liquidus temperature has been reached and then the casting process is triggered. According to another variant, an excess temperature increase is used as triggering criterion. According to a development of the invention, in both cases the current triggering criterion in each case (time or excess temperature increase) is measured and stored during each casting process. If after the casting and cooling it is found that a faultless casting result has been obtained, the stored values of the triggering criterion can be called up and used as nominal value for triggering the casting process during later melting and casting processes. According to a development of the invention, all temperature values are stored as a function of time during the entire heating-up process up to the casting time. Thus, the "temperature curve" is stored. During subsequent melting processes, a temperature curve is obtained the accurate variation of which depends on many parameters such as, for example, type of alloy, quantity and so forth. The curve variation then currently measured is compared with the stored curve variations. This can be done continuously or section by section. If then the measured curve corresponds to one of the stored curves within predetermined tolerances, the stored curve is identified and used as nominal value for the further heating-up. Thus, as soon as one of the stored curves has been identified, the further heating-up and casting process is only controlled in accordance with this curve.

In development of this variant, it is also provided to print out the actual values of the temperature curve and other measured or entered parameters. As a result, the dental laboratory and/or the dentist has clear proof of the "prehistory" of the cast object in dental engineering.

Attention must also be paid to the fact that the quantity of the melting charge is also a parameter which influences the casting result. Thus, for example, if the quantity is relatively large, it must pass as slowly as possible through the melting interval. In addition, if the quantity is relatively large, the excess temperature increase past the liquidus temperature must be a little greater in order to compensate for the cooling of the melt occurring during the casting in relation to the casting time needed with a relatively large quantity. According to a development of the invention, the quantity of the material to be melted is determined in a surprisingly simple manner by measuring the value of the power consumed by the induction coil and thus also induced by it in the melting charge. For this purpose, the current supplied to the induction coil is measured with the supply voltage being kept constant. This measured value is used as a correction value for the control system. In particular, the values for the triggering criteria (time or temperature increase) are appropriately reduced or increased.

In the text which follows, the invention is explained in greater detail with the aid of illustrative embodiments and in conjunction with the drawing, in which.

Figure 1:
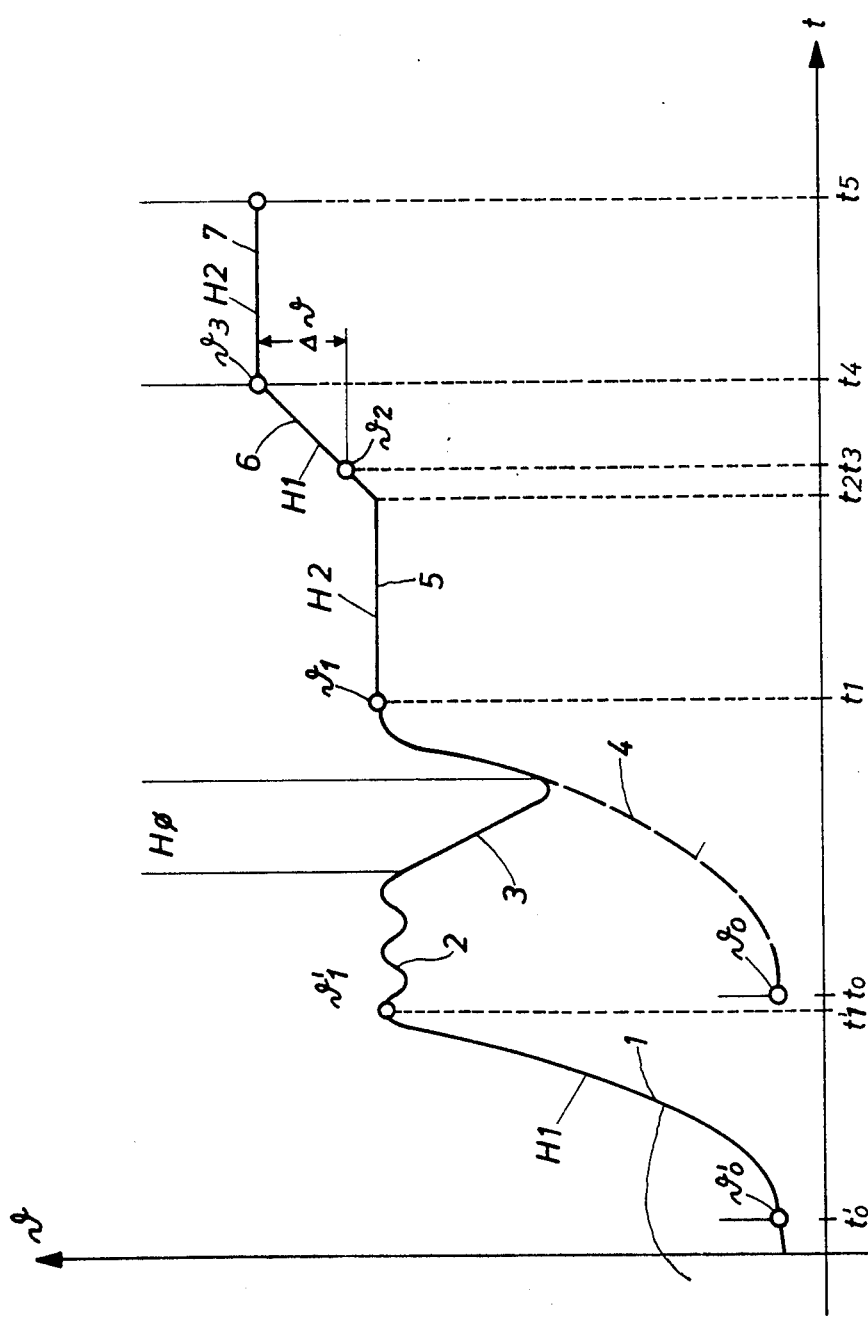
FIG. 1 shows the temperature variation of the melting charge in the method according to the invention during casting in the atmosphere.

FIG. 1 shows a diagram of the temperature $\theta$ against time t. Before the heating system is switched on, the melting charge is at the temperature $t_0$ (time $t_0$, $t'_0$). For the preliminary annealing, known per se, the induction coil is operated with full heating power H1. The temperature of the melt rises relatively rapidly, that is to say steeply, which is shown in curve section 1. At time $t'_1$, the solidus temperature $\theta_1$ is reached, that is to say first alloy components change from solid phase to liquid phase. In spite of the full heating power H1, the temperature no longer rises as steeply as previously at this time and, instead, the temperature curve changes to a flat section. When $\theta_1$, the solidus temperature, is reached, a flattening is seen in the curve H1. Thus, the differential quotient $d\theta dt$ is smaller than a nominal value. During preliminary annealing, the heating system is periodically switched on and off to keep the castings at the temperature reached. The heating is controlled by measuring the radiation intensity (corresponding to $\theta_1'$). The oscillating temperature variations shown are the result of the heating system being switched on and off. This so-called "preliminary annealing" is important so that all castings close to the solidus temperature are brought to the same temperature.

After a predetermined period of time has elapsed after the solidus temperature $\theta'_1$ is reached, the preliminary annealing is ended, that is to say the heating system is switched off (heating power HO). At that point, it is also possible to place a casting muffle into the casting device. Because the heating power has been switched off, the temperature drops again a little which is shown in curve section 3. Next, the heating system is switched on fully again, that is to say to heating power H1. A relatively steep temperature rise follows until the temperature curve flattens at time $t_1$ and the solidus temperature $\theta_1$ is again reached. This is recognised by the fact that the rise with time or, more accurately, the differential quotient $d\theta dt$ drops below a predetermined value. At this point, the beginning of the melting interval has been reached.

If heating is done without preliminary annealing, the power is increased from time $t_0$ and temperature $\theta_0$ along the dashed line 4 until the solidus temperature $\theta_1$ is reached.

To extend the melting interval, the heating power is switched to a lower value H2 at time $t_1$ so that the temperature changes only very slightly. This is shown by curve section 5. The stretching of the melting interval enables a homogenous temperature distribution to be achieved and all alloy components are able to change from solid to liquid phase. This is reached at time $t_2$ whereafter the temperature rises again in spite of the fact that the heating power H2 is still reduced. This rise is clearly identified at time t3 since the differential quotient of the temperature variation has exceeded a certain threshold value again. The temperature $\theta_2$ existing at this time $t_3$ represents in first approximation the liquidus temperature which indicates the end of the melting interval. This temperature $\theta_2$ is stored whereupon the heating system is again switched to full heating power H1. The temperature continues to rise according to curve section 6. Once the temperature of the melt has risen by a predetermined fixed value $\Delta\theta$, starting from the liquidus temperature $\theta_2$, and the temperature has reached the value $\theta_3 = \theta_2 + \Delta\theta$ at time $t_4$, the desired casting temperature $\theta_3$ has been reached. A signal indicating the readiness for casting (designation "green" in FIG. 1) is then generated and, at the same time, the heating power is again switched to a lower value H2 which is selected in such a manner that the temperature does not further increase (curve section 7).

A "casting interval" is then established, that is to say the casting process must be concluded within a fixed period of time $(t_4 - t_5)$ after the casting temperature $\theta_3$ has been reached. In the actual circuit, a timer is started for this purpose which, after a predetermined period of time has elapsed, generates a warning signal (designated by "red" in the drawing) which indicates that the casting time has elapsed.

FIG. 1 shows that, in contrast to the state of the art, a permanently preset casting temperature is no longer used in the invention; rather, this casting temperature is determined as a relative value from the temperature variation of the casting charge. Independently of the alloy to be melted in each case, the optimum casting temperature is thus automatically determined.

Figure 2:
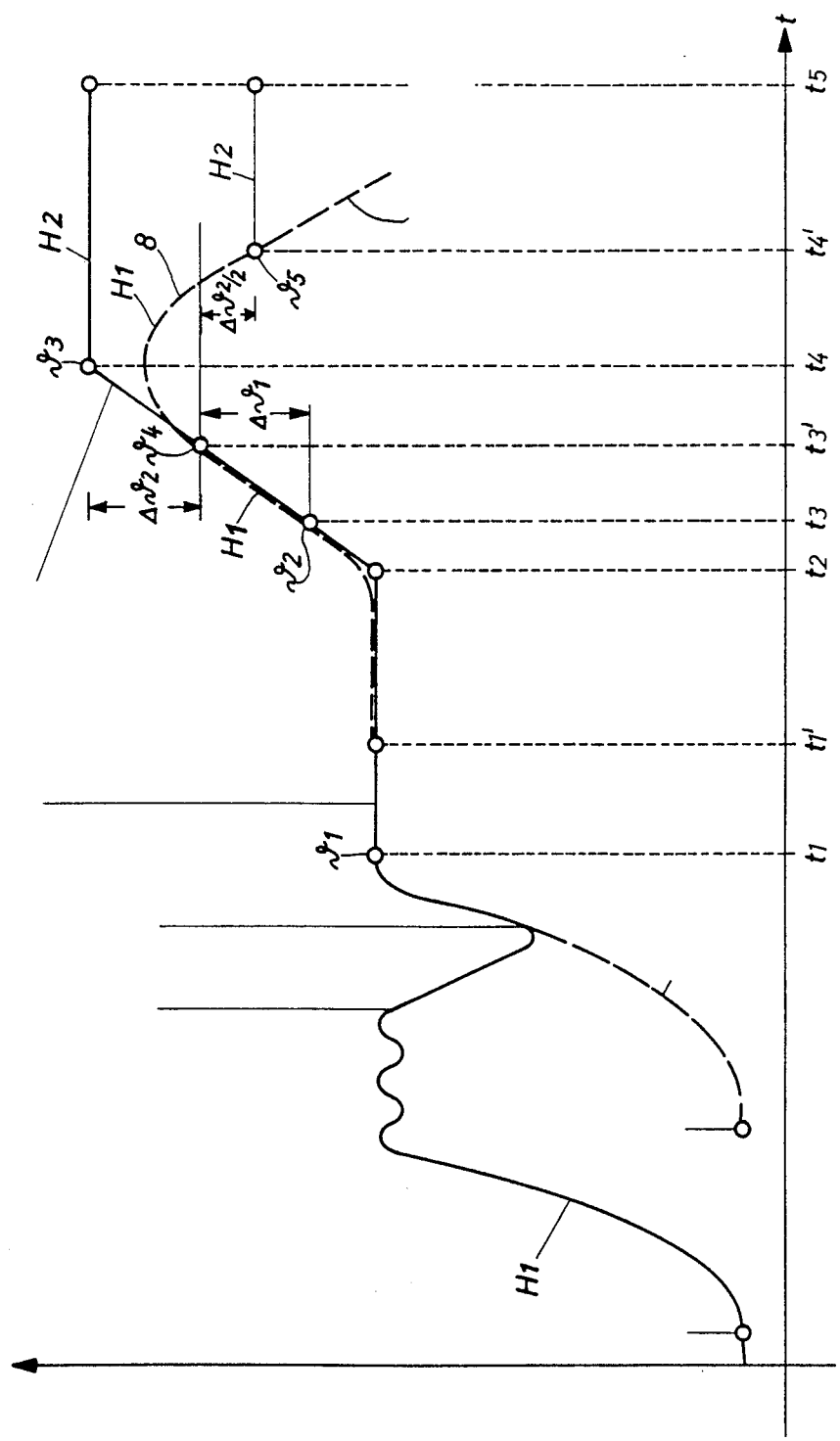
FIG. 2 shows a similar temperature variation during casting in vacuo.

FIG. 2 shows a similar temperature curve for casting in vacuo. In this case, however, the effect can occur that an oxide layer breaks open after further heating-up above the liquidus temperature $\theta_2$. If infrared radiation sensors are used for measuring the temperature, the breaking open of the oxide layer causes the radiation intensity to change despite the fact that the temperature is continuing to rise. The radiation intensity measured by the infra-red radiation sensor follows the dashed curve section 8. Thus it could occur that the temperature interval $\Delta\theta$ of FIG. 1 is not detected by measurement.

For this purpose, it is provided that at a predetermined period of time $t_{3-t3'}$ after reaching the liquidus temperature $\theta_2$, that is to say after the temperature has increased by a value $\Delta\theta_1$, the current temperature $\theta_4$ existing at this time $t_3'$ is stored. If the oxide layer does not break open, the process proceeds as described in connection with FIG. 1, that is to say a further temperature increase $\Delta\theta_2$ occurs until the casting temperature is reached at the temperature $\theta_3$. If, in contrast, the oxide layers do break open, the temperature varies along the dashed line 8. To be able to differentiate between these two variations, this temperature is then continuously monitored to see whether, after the stored temperature $\theta_4$ has first been reached at time $t_3'$, it (apparently) drops below this temperature again. If this is the case, the apparent temperature is allowed to drop further by a predetermined amount $\Delta\theta_2/2$, starting from the value $\theta_4$, and the temperature value $\theta_5$ is reached at time $t'_4$. At this time, the apparent casting temperature $\theta_5$ is then detected, the heating power is switched to the reduced value H2 and the casting signal is generated whereupon a casting interval $(t_4 - t_5)$ is again predetermined.

In the illustrative embodiment shown, the value $\Delta\theta_2/2$, by which the temperature is allowed to drop from the value $\theta_4$ to the apparent casting temperature $\theta_5$, just corresponds to half the temperature difference $\theta_2$ by which the temperature increases, starting from $\theta_4$, if an oxide layer is present, until the casting temperature $\theta_3$ is reached. However, it must be expressly pointed out that it is a pure coincidence that the value of $\Delta\theta_2/2$ just corresponds to half the temperature difference $\theta_2$. It can also be larger or smaller. The value which is optimum for this in each case is empirically determined by tests.

The other curve sections of FIG. 2 correspond to those of FIG. 1 so that no further explanation is necessary.

Figure 3:
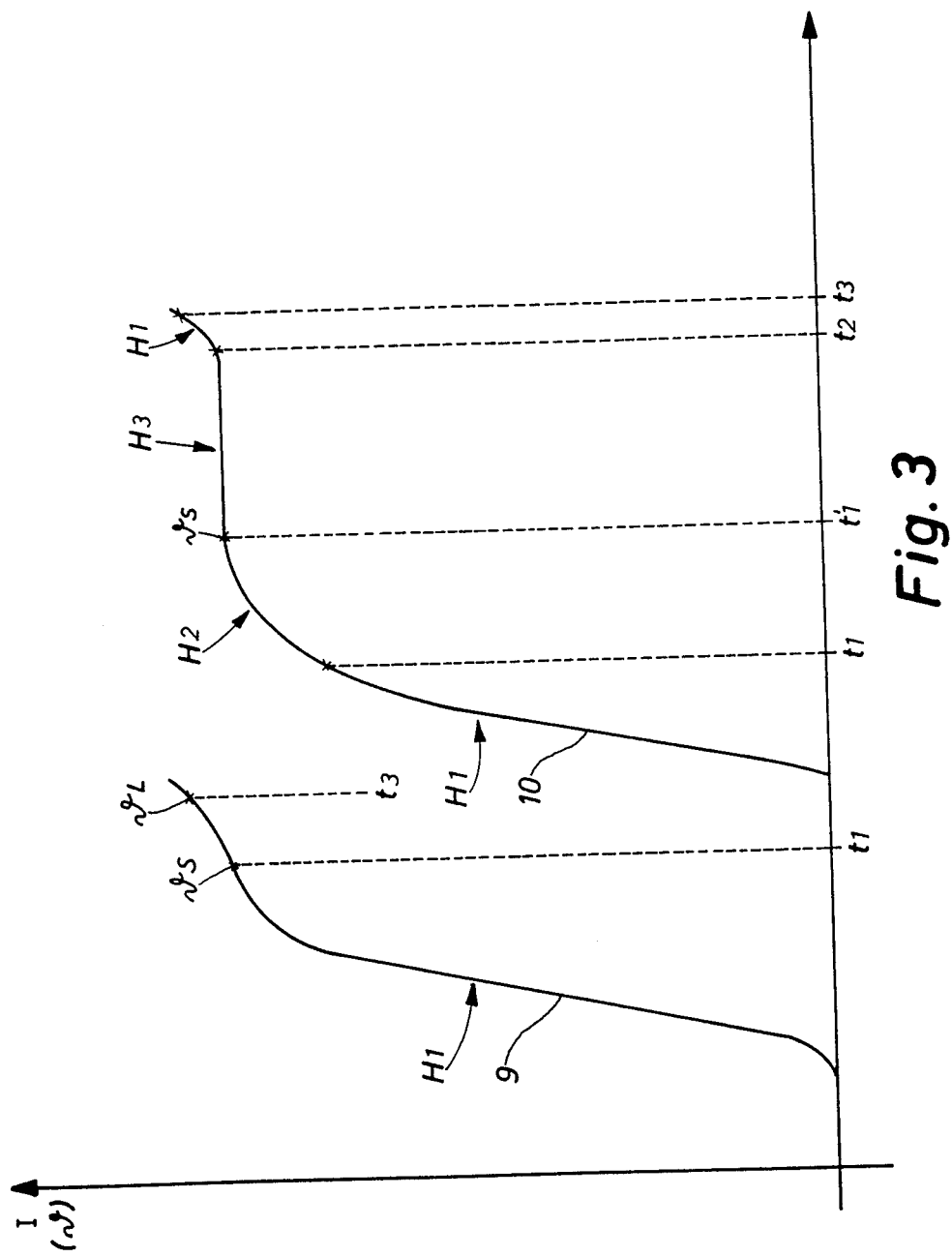
FIG. 3 shows two comparative curves of the temperature variation with a normal and an extended melting interval.

FIG. 3 shows more clearly the stretching of the melting interval. If the temperature is raised with full heating power H1 according to curve 9, no distinct horizontal section can be recognised in the temperature curve with some materials or alloys. As is shown by curve 9, the temperature between the solidus temperature $\theta_S$ and liquidus temperature $\theta_L$ varies with a clear gradient between times $t_1$ and $t_3$, the time interval for passing through this temperature difference being relatively short. As has been mentioned above, an inhomogeneous temperature distribution or non-uniform heating due to the skin effect can quite easily produce the effect that not all alloy components are already in the liquid phase, particularly in the interior of the melting charge, even though the radiation sensor which, of course, essentially measures the surface temperature, already indicates the liquidus temperature. This harmful effect can be eliminated by switching the heating power over. The switching from full heating power H1 (for example with 220V) to reduced heating power (of, for example 160V) has been discussed in conjunction with FIGS. 1 and 2. In curve 10 of FIG. 3, three different heating powers H1 (for example 220V), H2 (for example 200V) and H3 (for example 160V) are used. If the slope of the temperature curve at time $t_1$ is slowing down with full heating power H1, that is to say if the differential quotient $d\theta dt$ drops below a predetermined positive threshold value at time $t_1$, the heating power is first switched to the lower step H2. The temperature curve then enters more flatly into the horizontal section which begins at time $t_1'$ at the solidus temperature $\theta_s$. Next, the heating power is switched to an even lower heating power H3, thus passing through the favourable horizontal temperature curve section. The solidus temperature is detected by the fact that the differential quotient $d\theta dt$ reaches a second smaller threshold value, for example zero. If the temperature curve begins to rise again at time $t_2$ after passing through the horizontal section, the process progresses as described in connection with FIGS. 1 and 2, that is to say the heating power is switched to full heating power H1 again at time $t_3$.

Figure 4:
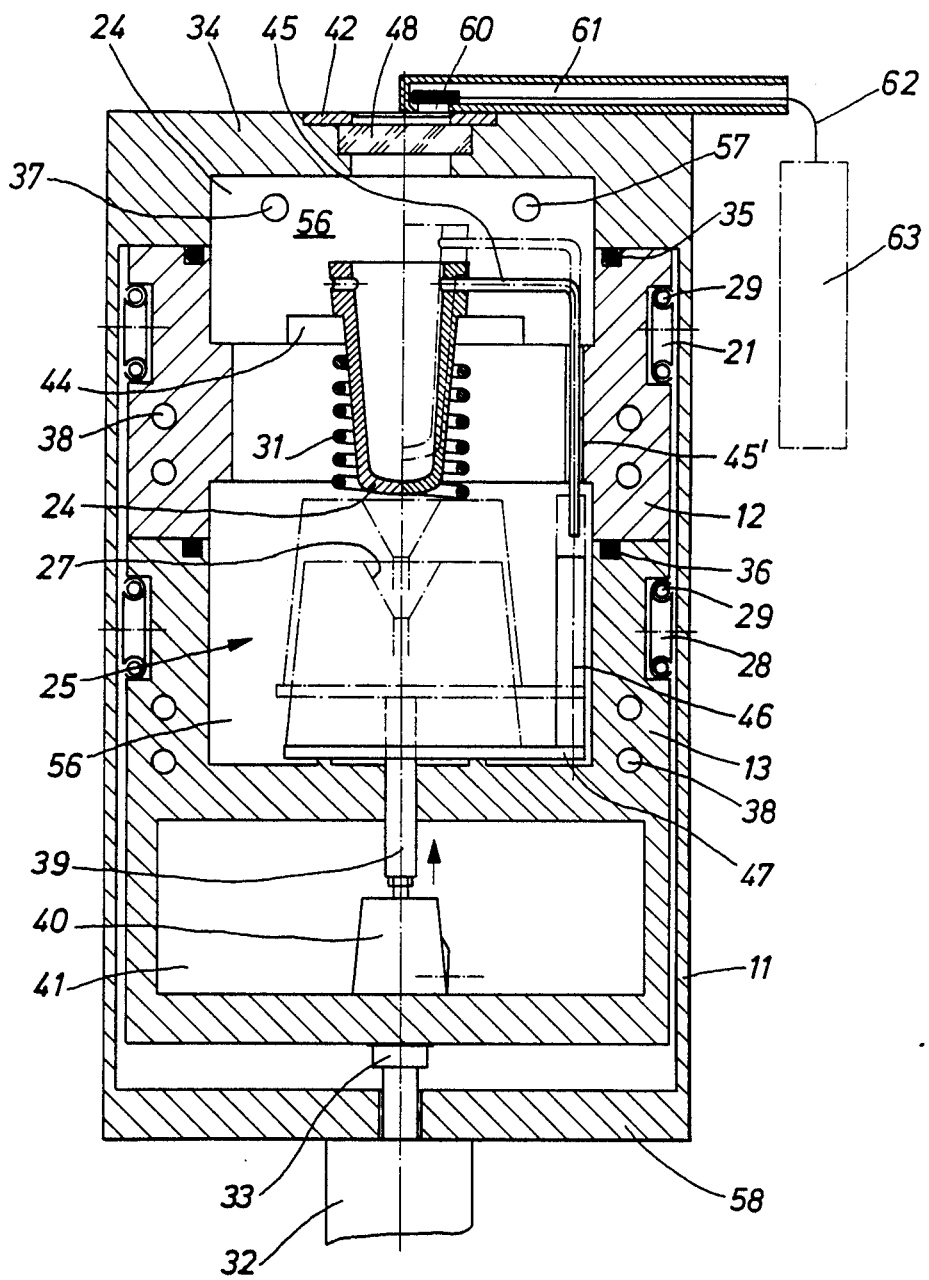
FIG. 4 and FIG. 5 show two illustrative embodiments of casting devices in which the invention is applied.

In the text which follows, reference is made to FIG. 4. In this figure, a casting device is shown in which the present invention can be applied. This casting device essentially corresponds to the casting device of German Offenlegungsschrift No. 2,305,418,5, with exception of the parts necessary for carrying out the method according to the present invention. FIG. 4 essentially shows a vertical section through a casting device. A frame support structure 11 is essentially constructed in the form of a box but is open at its front for moving sliding parts 12 and 13 in and out. The upper part of the frame support structure 11 is provided with a reinforced cross bracket 34 having a U-shaped section pointing downwards. The horizontal abutting ends of this section are located opposite to the top of the upper sliding part 12 which has an essentially H-shaped cross-sectional profile. In the cross bar of this H-shaped section, a recess is provided into which a crucible 24 can be inserted. Around approximately the lower half of the crucible 24, an induction coil 31 is arranged at a certain distance from the crucible 24 and, in conjunction with a high-frequency generator (not shown) provides for the melting charge in the crucible 24 to be heated up. The crucible 24 is acutely conically tapered from top to bottom and has in the area of its upper end a circumferential shoulder or a collar which rests on a holding ring 44. The holding ring 44 is supported at the top of the cross bar of the H-shaped cross-sectional profile. The upper sliding part 12 can be displaced with respect to the supporting structure 11 in lateral guide rails 21. It is supported via ball bearings 29 having sufficient play to allow a vertical displacement of the sliding part 12. In this respect, there is sufficient play so that the sliding part 12 can be displaced far enough in the direction of the upper cross bracket 34 so that the abutting ends of the sliding 12 and of the cross bracket 34, which are allocated to each other, can be brought into firm contact with each other, in which arrangement the sealing 35 provided in a groove at the top of the sliding part 12 provides for a tight seal between the upper cross bracket 34 and the upper sliding part 12, which can be loaded with over- or under-pressure. In the wall of the sliding part 12, one or more coolant lines 38 can be provided through which coolants, for example water, are conducted.

Below the sliding part 12, a lower sliding part 13 is arranged which can also be displaced in ball-bearing-supported guide rails 28. Here, too, the ball bearing 29 has a play which permits vertical displacement of the sliding part 13. The sliding part 13 has an essentially U-shaped cross-sectional profile which allows a casting muffle 25 to be accommodated in its interior space. The top of the sliding part 13 forms an abutting end which can be brought into contact with the underside of the upper sliding part 12. Here, too, a sealing 36 is inserted into a groove at the abutting end of the lower sliding part 13. The lower sliding part 13 can be vertically displaced by a piston/cylinder arrangement (cylinder 32 and piston 33) which is supported at a lower cross bracket 58 at the underside of the frame support structure 10. If the lower sliding part 13 is raised by the piston/cylinder arrangement 32, 33, it presses against the upper sliding part 12 as a result of which the latter is also raised until it stops against the upper cross bracket. The upper cross bracket 34, the upper sliding part 12 and the lower sliding part 13, in conjunction with the sealings 35 and 36, form a chamber 56 which can be evacuated or charged with compressed gas. This chamber 56 therefore accommodates the crucible 24 and the casting muffle 25 and thus forms a melting and casting space. In the upper cross bracket, openings 37 and 57 are provided via which the chamber 56 can be linked to a vacuum pump or to a compressed-gas source.

In addition to the lifting device formed by the piston/cylinder arrangement 32, 33 and used for closing the casting device, another lifting device formed by piston/cylinder arrangement 39, 40 is provided which is used for raising and lowering the casting muffle 25 and for simultaneously opening or closing the crucible 24. The piston/cylinder arrangement 39, 40 is arranged in a recess 41 in the lower area of the sliding part 13. In this arrangement, the piston rod 39 projects through the bottom wall of the sliding part 13 and is mounted on a support plate 47 which carries the casting muffle. The casting muffle can thus be displaced between two limit positions, the upper limit position shown with dashed lines being used for the casting process. In this connection, a filling funnel 27 of the casting muffle 25 comes to be located closely below the outlet opening of the crucible 24. The support plate 47 is elongated to one side (right-hand side in FIG. 4) to form a link arm to which a vertical lifter 46 is attached. Thus, by raising the casting muffle 25, the lifter 46 is also raised. When the sliding parts are closed, this lifter 46 is flush with another lifter 45' which is carried in an opening in the cross part of the H-shaped crosssectional profile of the sliding part 12 and opens into a horizontal lifting arm 45 which is mounted in a hole in one of the crucible parts. The ends, facing each other, of the two lifters 45' and 46 are at a distance from each other in the lower limit position of the piston/cylinder arrangement 39, 40. As a result, a lost motion is created which ensures that the two lifters 45' and 46 come into contact with each other only shortly before the upper limit position of the casting muffles 25 is reached and then provide for the crucible 24 to open during the last portion of the upward movement of the casting muffle 25. Above the crucible 24, the cross bracket 34 has an opening which is closed by a viewing window 48. The viewing window 48 is mounted by means of a holding ring 42. Above the viewing window, a temperature sensor in the form of an infra-red radiation sensor 60 is attached. The sensor 60 and its feed lines 62 are held at the upper cross bracket 34 by means of a holder 61. The feed lines 62 lead to a control device 63 which also controls, for example via solenoid valves, the piston/cylinder arrangement 39, 40 which triggers the casting process. Thus, when the optimum casting temperature has been reached in accordance with the method described above, the casting process can proceed automatically in this case.

Figure 5:
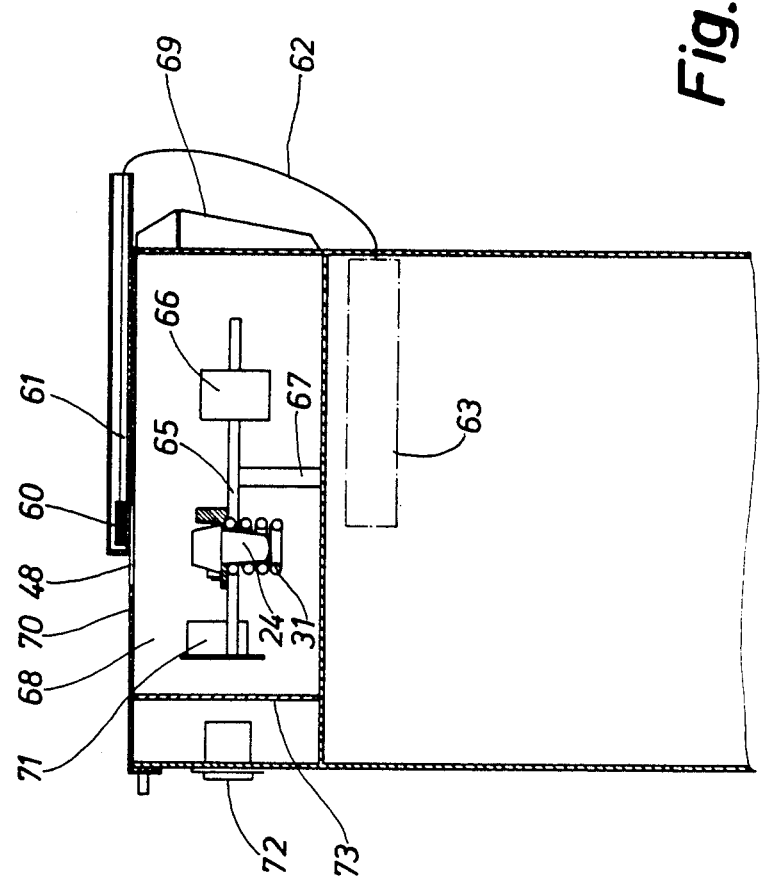

FIG. 5 shows another casting arrangement in which the invention can be used. In this case, crucible 24 and heating device 31 are mounted at a rotating arm 65 which has a counter-weight 66 and can be rotated around a vertical axis 67. This is a centrifugal casting arrangement comprising a centrifugal space 68 which is accessible from the top since its housing cover 70 can be opened via a hinge 69. 71 Designates a receptacle for a casting mould. A control desk 72 is isolated from the centrifugal space 68 by a dividing wall 73.

Figure 6:
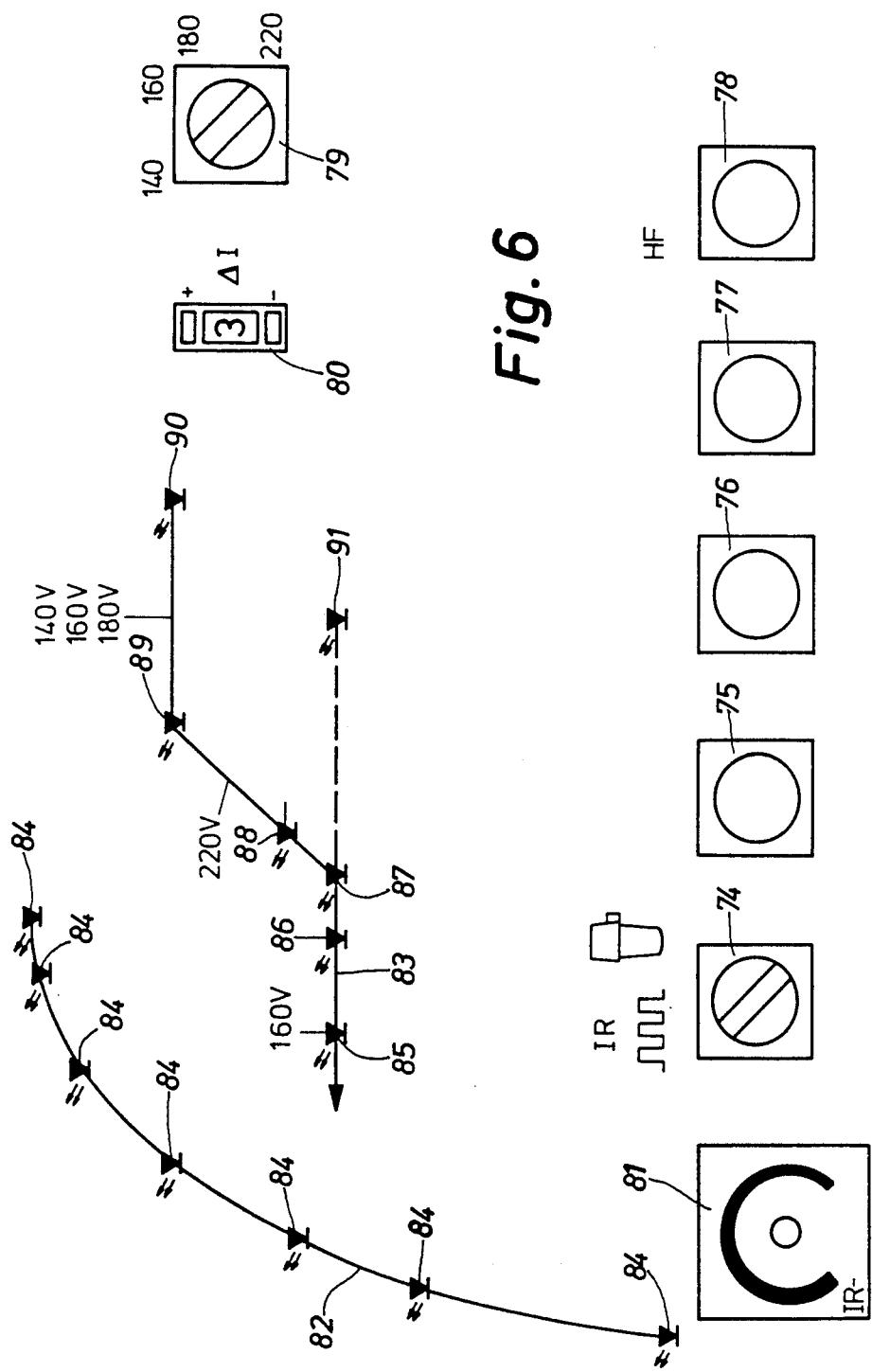
FIG. 6 shows a diagrammatic view of an operating panel for the arrangement according to the invention.

FIG. 6 shows a section of the control desk of the device according to the invention. Various control function switches or keys are provided. Initially, two operating modes can be selected by means of a switch 74. On the one hand, the operating mode in which the casting process is triggered when a casting temperature preset at the control knob 81 has been reached, and the operating mode in which the casting temperature is automatically determined in accordance with the invention. A key 75 is used for starting the process of preliminary annealing described in conjunction with FIG. 1. A key 76 is used for starting the process without preliminary annealing (curve section 4) described in conjunction with FIG. 1. Key 77 can be used for manually triggering the casting process. The heating system can be switched off at any time, even during the automatic sequence, by means of a key 78.

A switch 79 can be used for preselecting various heating steps for the heating power when the casting is reached. The temperature difference $\Delta\theta$ according to FIG. 3 can be preselected via an actuator 80.

Next, two temperature curves 82 and 83 are provided along which are associated with light-emitting diodes 84 to 91 are arranged. These light-emitting diodes indicate to the operator the curve section in which the temperature is located in each case. If the first operating mode is selected via the switch 74, the temperature varies along the curve 82, whereupon the corresponding diode 84 lights up as a function of the temperature reached in each case until the last diode lights up when the final temperature preset at the control knob 81 is reached.

If the second operating mode with automatic determination of the optimum casting temperature is selected, the temperature initially also varies along curve 82. When the solidus temperature $\theta_S$ is reached, diode 85 lights up. If the process is still in the melting interval some time after this temperature has been reached, diode 86 lights up. When the temperature begins to rise again at the end of the melting interval, diode 87 lights up and, after the temperature $\theta_2$ is reached, diode 88. When the casting temperature $\theta_3$ is reached, diode 89 lights up, in green colour in this case. At time $t_5$, that is to say after the casting interval has elapsed, the red diode 90 lights up. As soon as diode 89 lights up, the operator must therefore press key 77. If, on the other hand, diode 90 lights up, he can see that he must no longer trigger the casting process.

If operational disturbances occur during the automatic sequence, in particular, if the temperature does not clearly rise after having passed through the melting interval, the lighting-up of diode 91 after a predetermined period of time has elapsed indicates that the maximum time has been exceeded without the casting temperature having been reached. The melting process must then be aborted.

Figure 7:
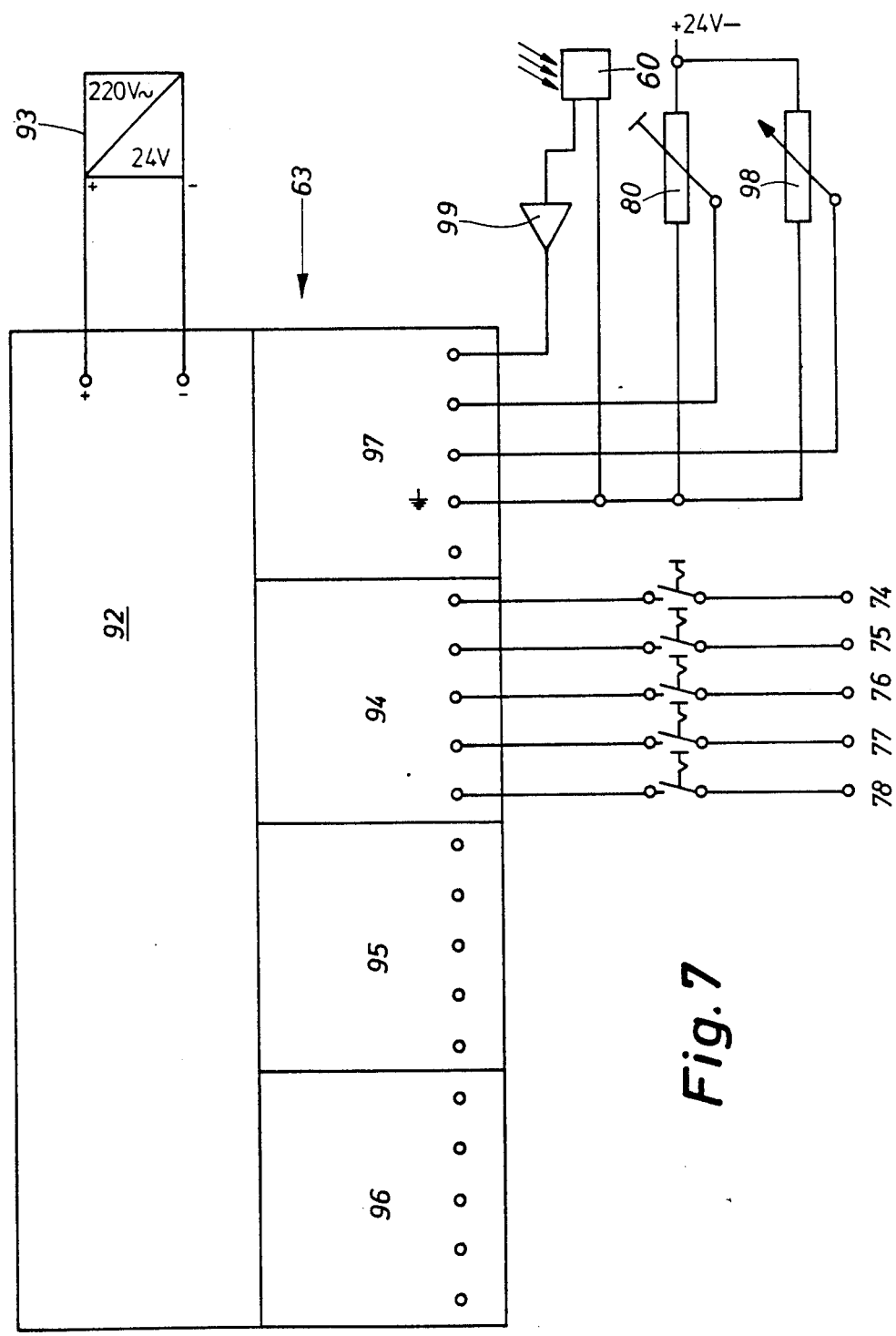
FIG. 7 shows a block diagram of the control unit of the arrangement according to the invention.

FIG. 7 shows a block diagram of the control unit 63. The heart of the control unit is a microprocessor 92 which is supplied with mains voltage via a transformer 93. One of the outputs 95 or 96 of the microprocessor switches a relay which drives, via switch 79, the correct heating power after the casting temperature has been reached. The microprocessor has several inputs 94 which are connected to the switches or keys according to FIG. 6 as indicated by reference symbols 74 to 78 which refer to the switches and keys of FIG. 6.

In addition, the microprocessor has several outputs 95 and 96 which, on the one hand, drive the light-emitting diodes 84 to 91 and, on the other hand, switch the various power steps for the heating power, completely switch off the heating power and/or drive actuating elements for triggering the automatic casting.

As another input for the microprocessor 92, an analogue/digital convertor 97 is provided the inputs of which are supplied with the following signals: firstly the output signal of the infra-red radiation sensor 60 which, if necessary, is further amplified via an amplifier 99; then a signal from a potentiometer 80 (compare also FIG. 6) which is used for presetting the temperature difference $\Delta\theta$ according to FIG. 1, or, more accurately, a predetermined value $\theta_I$ for the output signal of the sensor 60, this signal corresponding to the value $\Delta\theta$ according to the radiation/current or voltage characteristic of the sensor. Finally, the absolute value of the casting temperature can also be set via a potentiometer 98, which corresponds to the control knob 81, in the operating mode according to curve 82 of FIG. 6.

The microprocessor 92 continuously analyzes the analog/digital-converted signal from the sensor 60, forms the differential quotient or, more accurately, the difference quotient for determining the slope of the temperature curve, carries out the comparison operations described, calculates, if necessary the correction values described and generates the various control signals at its outputs. For this purpose, the microprocessor, as usual, contains arithmetic units, data memories, program memories and in the case of the blocks for the outputs 95 and 96, the corresponding driver circuits. After the explanations given above, a specialist is easily able to program the microprocessor in such a manner that it carries out the method steps described.

Figure 8:
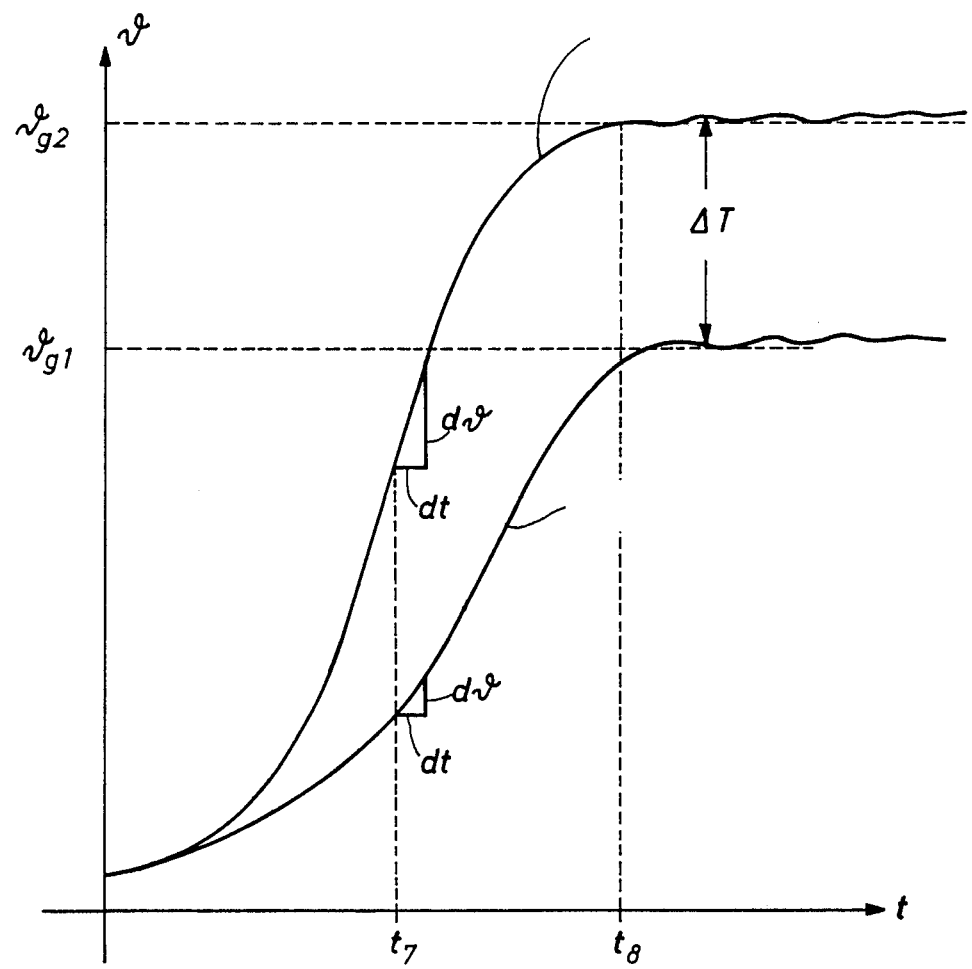
FIG. 8 shows the temperature variation with old and new carbon crucibles.

FIG. 8 shows temperature variations of old and new crucibles which can be automatically differentiated according to the invention. Normally, alloys are melted in ceramic crucibles whereas gold is melted in a carbon crucible which is inserted into a ceramic crucible. Carbon crucibles show different radiation intensities at the same temperature, new unused crucibles having a lower radiation intensity (darker radiation) than older crucibles used several times. When temperature is measured by means of an infra-red radiation detector, this would entail a falsification of the measurement result.

To avoid this error, the slope of the curve is determined during the first heating-up phase, that is to say before the liquidus temperature is reached. In detail, the slope of the curve is determined by forming the differential quotient $d\theta/dt$ (of the difference quotient in digital technology) a predetermined period of time after the full heating power has been switched on, that is to say at time $t_7$ in the example of FIG. 8. This value is compared with a predetermined threshold value. If the slope value determined is below the threshold value, a new crucible is present whereas an old crucible is recognised in the opposite case. Test measurements have shown that in the temperature range of interest for the casting temperature (for example 1500° C.), the output signal of an infra-red radiation sensor differs by a relatively constant value $\Delta T$ for old and new crucibles. By adding or subtracting this value $\Delta T$, the two curves of the FIG. 8 can be transformed in such a manner that a single corrected curve can be used for both cases. If the curve for the old crucible is selected as the determining curve and, accordingly, the casting temperature is set for the value $\theta_g 2$, it is only necessary to add the value $\Delta T$ to the output signal of the infrared sensor if the presence of a new crucible has been detected as described above. If the output signal of the infra-red radiation sensor reaches the value $\theta_g 1$, the addition of $\Delta T$ signals the value $\theta_{g2} = \theta_{g1} + \Delta T$ to the microprocessor, which value is then recognised as the preset value for the casting temperature.

Conversely, the curve for the new crucible could naturally also be used as reference curve. In this case, the value $\Delta T$ would have to be subtracted from the output signal of the sensor if an old crucible is detected, in which case, naturally, the value $\theta_{g1}$ would have to be stored as the threshold value for detecting the casting temperature.

The following values have proved to be favourable values for individual variables described above: for heating an induction coil, 220V are used at the higher heating power H1. For the heating power H2 of FIG. 3 (gentle entering into the melting interval) 200 and 180V, respectively, have been found to be favourable. For the heating power H3 during the melting interval and also during the casting interval (heating power H2 of FIG. 1) 160V are recommended.

100° C. is appropriate as temperature difference $\Delta\theta$ (in FIG. 1) for overheating the melting charge past the liquidus temperature.

The voltage values specified above by way of example relate to a series transformer for driving the high-voltage transformer for the high-frequency heating system (HF generator).

Figure 9:
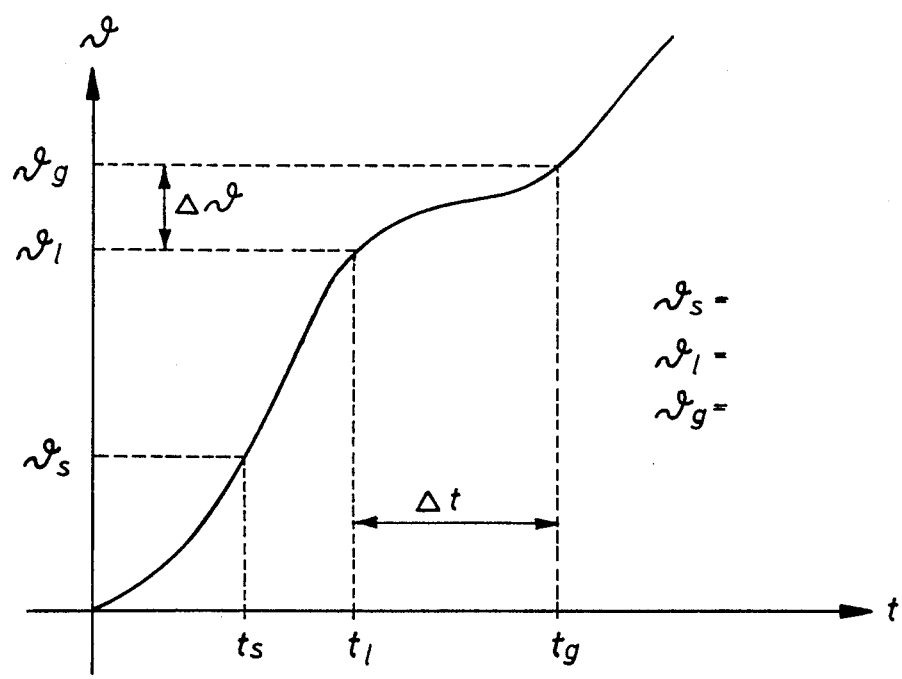
FIG. 9 shows the temperature variation of the melting charge with an indistinctly defined melting interval as occurs, for example, in the case of gold alloys.

FIG. 9 shows a temperature curve (temperature against time) similar to the curve shown on the left-hand side in FIG. 3. In contrast to this curve, the liquidus temperature $\theta_s$ is reached or even exceeded in FIG. 9 when the curve displays a flattening such as, for example, in the case of cold alloys. According to a variant of the invention, the point where the liquidus temperature ($\theta_1$) is reached is determined by the fact that the differential quotient $d\theta dt$ is smaller than a predetermined nominal value. The time at which the liquidus temperature is reached is designated by $t_1$ in this case. The casting time $t_g$ is then determined by the fact that heating is continued with constant heating power from time $t_1$ for a predetermined period of time $\Delta t$ which can be, for example, 22 s with a certain alloy, and then, after time $\Delta t$ has elapsed, the casting readiness signal is generated or the casting process is automatically initiated. Thus, the reference variable is the time when the liquidus temperature is reached and not the beginning of the heatingup process.

According to another variant of the invention, a temperature criterion can be used instead of a predetermined period of time. After the liquidus temperature $\theta_1$ is reached, heating is continued with constant heating power until a temperature increase by a preset value $\Delta t$ is reached which determines the casting temperature $\theta_g$.

Initially, the values of $\Delta t$ and $\Delta\theta$ are preset by the user, for example by entering them via a keyboard. Thus, initially these are empirical or intuitively predetermined values. It is quite possible that these can lead to favourable, but also to unfavourable casting re- sults.

According to a development of the invention, the casting values $\theta_g$, $t_g$, $\Delta\theta$ and $\Delta t$ are stored. In addition, value for two further parameters, for example of the type of the alloy to be melted are entered by the user. If the casting process last carried out in each case proves to be favourable, the user leaves the abovementioned stored values in the memory. If these values prove to be unfavourable, he deletes them. After several such "runs", the device only contains favourable values leading to optimum casting results in the memory. In future melting and casting processes, these casting values or the values $\Delta\theta$ or $\Delta t$ no longer need to be externally entered but can be called up from the memory. Thus, the user only needs to enter certain parameters which will be explained in greater detail below, from which the associated values optimum in each case are called up from the memories and are used for controlling or determining the casting time.

According to a development of the invention, the entire temperature curve is stored during each melting and casting process, for example in the form of pairs of temperature and time values. If after evaluation of the casting result a stored temperature curve proves to be favourable, it remains stored; otherwise it is deleted. After several runs, the memory will then contain a plurality of characteristic temperature curves. During subsequent casting and melting processes, the resultant curve will be compared with the stored curve variations. This already occurs continuously during the heating-up of the specimen to be melted. Naturally, instead of a continuous comparison, the comparison can also be carried out section by section. After some time, but at the latest when the liquidus point (time t1) is reached, an agreement (within predetermined tolerances) will be found between the measured curve and this stored curve, provided a sufficient number of curve variations have been stored. From this moment on, the further controlling and, in particular, the determining of casting time and casting temperature is effected via the one selected stored curve which is used as nominal value for closed-loop control. Thus, unambiguously reproducible casting results are always obtained without having to enter further parameters.

Figure 10:
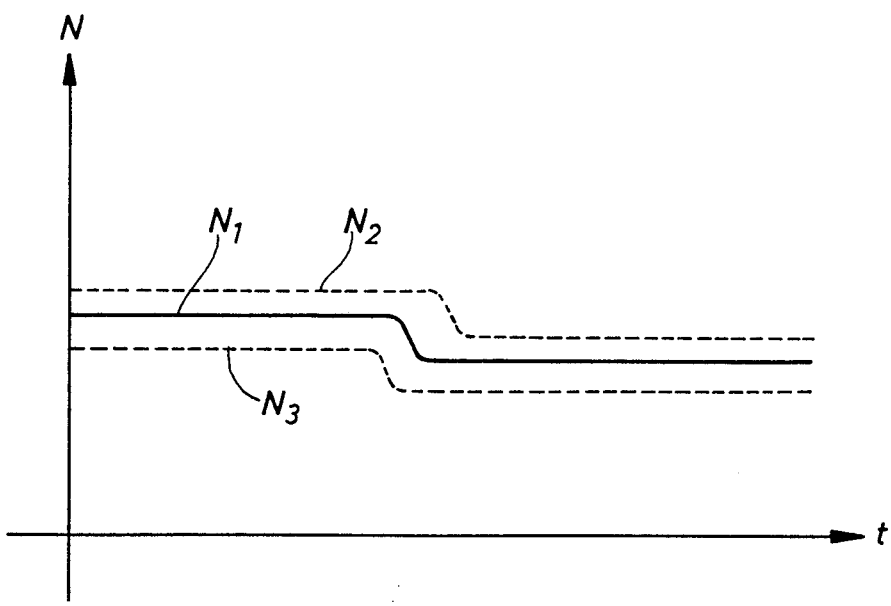
FIG. 10 shows the variation with time of the power induced by the induction coil in the melting charge (with constant supply voltage) for various quantities of the melting charge.

As has already been initially mentioned, the quantity of the material to be melted influences the casting result or the values of $\Delta\theta$ or $\Delta t$, respectively. According to a development of the invention which is explained below by referring to FIG. 10, this quantity is indirectly determined by measuring the current consumed by the induction coil (with constant voltage) or, expressed more generally, the power consumed by the induction coil and thus induced in the melting charge. With a relatively small quantity, the power is less than with a relatively large quantity at constant supply voltage. This is shown by curves $N_1$ to $N_3$ of FIG. 10 in which the variation of electric power against time is shown. The power drop of the curves, tested relatively, is explained by the effect, initially described, of the collapsing of the originally cube-shaped castings when the liquidus temperature is reached. As indicated in FIG. 10, the time when the liquidus temperature is reached can also be displaced for different quantities. However, the information of FIG. 10 in this respect is purely qualitative and also depends, among other things, on the arrangement of the casting cubes in the crucible. After the liquidus temperature is reached, the power curves are horizontal again. Conclusions on the quantity can be drawn from the absolute level of the power consumed in each case. This is then used for determining correction values for $\Delta\theta$ and $\Delta t$. For example, the predetermined or stored value is extended by a further amount if a large quantity is present (curve $N_2$ of FIG. 10) and the triggering criterion $\Delta t$ is used. Conversely, this value is reduced for a relatively small quantity (curve $N_3$). The same analogously applies to the triggering criterion $\Delta\theta$.

FIG. 10 shows that precise measurement values about the power consumed are already available at the beginning of the heating-up process. After this power measurement is available, a selection factor can therefore also be determined by which the temperature values measured are multiplied. The temperature values corrected in this manner can then be compared with the stored curves in accordance with the above illustrative embodiment. Thus, a separate curve does not need to be stored for any possible quantity of casting cubes or casting material. Rather, only a small number of characteristic curves need to be stored for each material which are then compared with the values corrected by the "quantity factor". This saves memory space.

Figure 11:
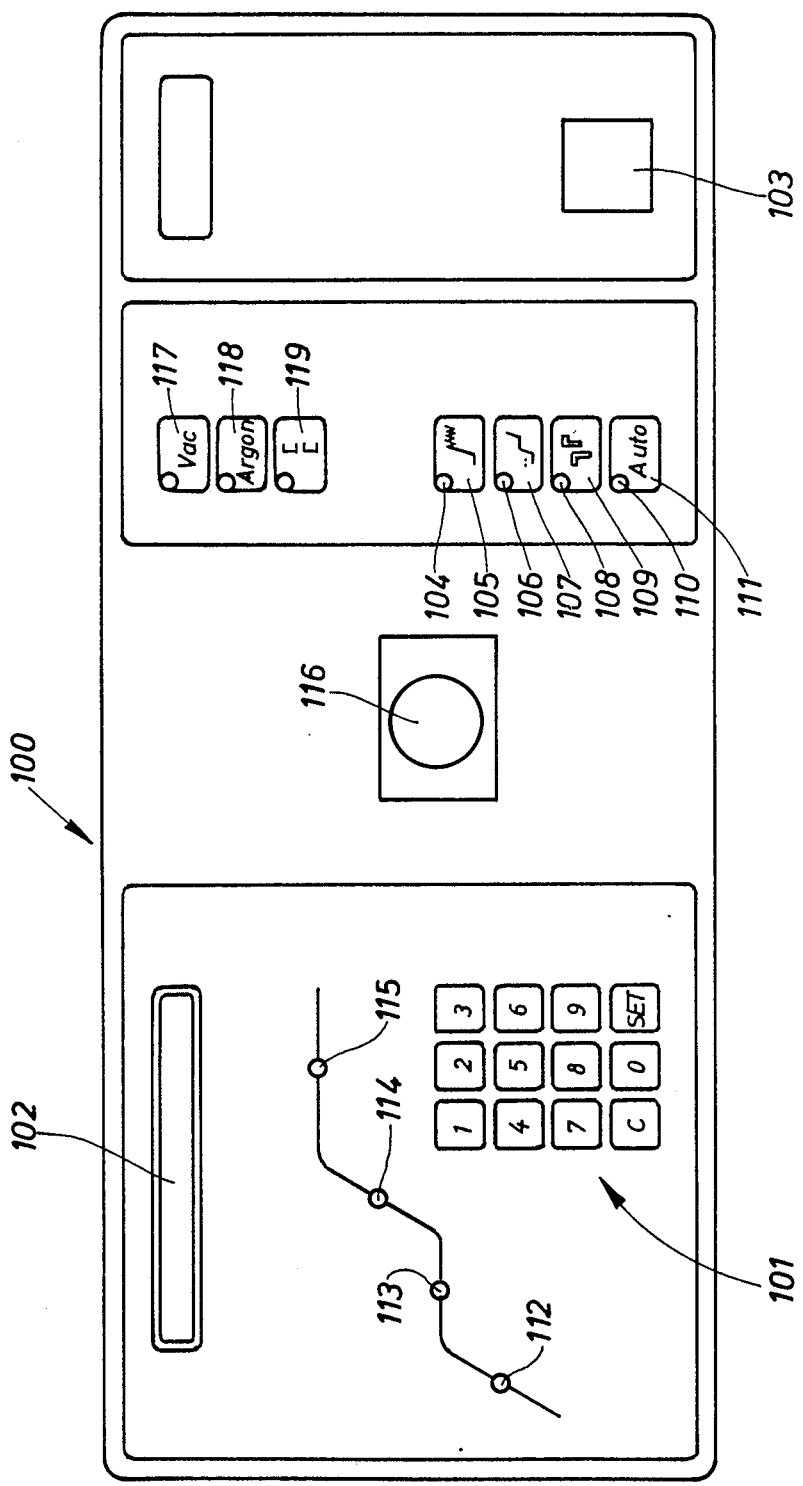
FIG. 11 shows another diagrammatic view of an operating panel for the arrangement according to the invention.

FIG. 11 shows the "switching panel" of another variant of the invention. In principle, the circuit used corresponds to that of FIG. 7. In contrast to the version of FIG. 6, "dialog operation" is now possible. The switching panel 100 has a normal key panel 101 comprising 10 keys for the digits 0-9 and a clearing key C and an input key which is designated by the term "set". Input values are sampled or operating steps are requested under control of the microprocessor 92 via a display 102 which consists, for example, of an LCD or a LED display. When the main switch 103 is switched on, the microprocessor 92 first starts a test program. Initially, this tests whether the casting device is connected to compressed air. For this purpose, a pressure sensor (not shown) is sampled. If its output indicates that no compressed air is available in sufficient quantity, the display 102 indicates that compressed air is missing, for example by indicating "compressed air". The operator can then initiate the necessary steps. If the test shows, if necessary after a corresponding intervention by the operator, that compressed air is present, a similar check shows whether cooling water is present and whether the device is closed, that is to say the "drawers" are closed. Here, too, a corresponding indication is given and the next step is carried out only after a satisfactory check of the particular preceding step. Next, the microprocessor 92 requests certain parameters to be entered by the operator. Firstly, it requests the input of a number, single-digit in this case, for the "basic program" via the display 102. Several basic programs for various alloys are given, for example for cobalt - chromium, nickel - chromium, precious metal alloys and so forth. Each of these basic programs is associated with a number to be entered by the user via the keyboard 101. The input is completed by pressing the "set" key. After a basic program has been called up, further parameters are requested. Thus, the question is put whether this is an alloy with or without oxide layer (compare FIG. 2); whether this is a melt in which the oxide layer breaks open. In addition, the period of time $\Delta t$ (FIG. 9) or the excessive temperature increase $\Delta \theta$ are also requested, depending on the "triggering criterion for the casting". Finally, the required power step for the heating system is also requested. After each request, the appropriate value is entered by the user via the keyboard 101 and stored by pressing the "set" key.

According to one version, the highest possible value for the individual parameters can be entered in each case if only the "set" key is pressed instead of entering a digit. Finally, the question can be put whether the curve variations occurring during the subsequent process are stored. These values are then allocated to certain memory areas which can be called up via an "address" appearing on the display 102. Thus, instead of entering the basic program and the individual parameters, the user can also directly enter a multi-digit "basic program number" which then calls up the values stored under this address. This simplifies the entering procedure.

After the "set" key has been pressed after all values requested have been entered, the automatic heating process starts. The indication "start" appears on the display 102. The machine is charged and after the drawer has been opened and subsequently closed, the question is put whether preliminary annealing is to be carried out (compare FIG. 2). For this purpose, a light-emitting diode 104 flashes at a key 105. The diode 104 is continuously lit after the key 105 is pressed. The induction heating is then switched on which is indicated by the diode 112 lighting up. The device then automatically runs through the preliminary annealing program. After completion of the preliminary annealing, the diode 104 flashes again and the command "insert muffle" appears on the display 102. The preheated casting muffle is fetched from a preheating furnace and inserted into the appropriate lower drawer. After actuation of the drawer, which is detected via switching contacts, the indication "start melting" appears on the display 102. Diode 106 flashes at a key 107. The melting process is initiated by pressing the key 107. Diodes 112, 113, 114 and 115 indicate that the process is passing through the melting curve.

As soon as readiness for casting is reached in accordance with the criteria described above, "casting" is indicated on the display 102. Diode 115 lights up and diode 108 flashes in the key 109. Pressing the key 109 triggers the casting process in that, in the illustrative embodiment described above, the two crucible halves are vertically displaced with respect to each other so that the molten charge can flow into the casting muffle located underneath. At this time, diode 106 is extinguished. Instead of manually triggering the casting, the casting can also be automatically triggered. For this purpose, key 111 must be pressed before starting the program, which is indicated by the diode 110 lighting up. When casting is finished, all parameters initially entered are indicated on the display 102. By pressing the "set" key, the values which actually occurred and were measured for detecting the readiness for casting can now be indicated.

The parameters which were entered by the user and which actually occurred are alternately indicated by further pressing of the "set" key to make it possible to obtain a comparison. It is then possible to store the parameter values which currently occurred in accordance with the memory option described above.

A restart is possible by pressing the clear key "C". The process then runs through the basic program as described above.

With certain basic programs (depending on the respective alloy), the "preliminary annealing" is not carried out. Similarly, certain basic programs can be used for preselecting whether stretching of the melting interval is to be used or not. Depending on the basic program selected, the casting triggering criteria described in detail above are also called up.

FIG. 11 also shows - as generally used - an inspection window 116 through which the melt can be observed. For other functions, keys or light-emitting diodes 117, 118, 119 are also provided by means of which, for example, vacuum can be switched on, protective gas can be fed in or compressed air can be applied to the casting space during casting or such conditions (including closed "drawers"can be signalled. Plug-in modules, for example in the form of "PROM's" can also be used for storing the various programs. Thus, the device can also be re-equipped with newly developed programs.

We claim:
1. Method for controlling the melting and casting process in precision casting under the control a heating system, particularly for dental engineering, comprising the following steps:
heating a melting charge by supplying thermal energy to the melting charge;
continuously measuring the temperature of the melting charge with respect to time; calculating the slope of temperature, i.e. the change with time ($d\theta/dt$) of the temperature $\theta$ of the melting charge;
generating, during supply of energy to the melting charge, a first signal at a time t1 when the slope deviates from an initially high value of slope greater than zero to a slope of substantially zero;
generating a second signal at a time t3 when the slope increases from the slope of substantially zero to a constant slope of substantially greater than zero wherein at time t1 the melting charge reaches the solidus temperature and at time t3 when all the melting charge changed from solid to liquid phase, and said higher value corresponding to a moment the temperature of the melting charge reaches the liquidus temperature; and generating a third signal at a time t3' for triggering the casting process, said third signal being delayed by a predetermined period of time with respect to said second signal.

2. Method according to claim 1, comprising:

measuring and storing actual values of the predetermined period of time in a first melting and casting process and, in subsequent melting and casting processes, using one of the stored actual values as nominal values for triggering the casting process.

3. Method according to claim 2, comprising:

storing the measure variation with time of the temperature during the entire heating-up process up to the time of casting in a 1st melting and casting process, and, during subsequent melting processes, comparing the variation with time of the temperature measured continuously or section by section with the stored values and, if agreement exists within predetermined tolerances between a stored and a measured variation, controlling the time of casting and/or the casting temperature as a function of the casting data of the stored variation.

4. Method according to claim 1 wherein the heating system is constructed as an induction coil, comprising measuring the electric power consumed by the induction coil and varying the generation of the third signal as function of the measured power.

5. Method for controlling the melting and casting process in precision casting under the control of a heating system, particularly for dental engineering, comprising the following steps:

heating a melting charge by supplying thermal energy to the melting charge;

continuously measuring the temperature of the melting charge with respect to time;

calculating the slope of temperature, i.e. the change with time $(d\theta/dt)$ of the temperature $\theta$ of the melting charge;

generating, during supply of energy to the melting charge, a first signal at a time t1 when the slope deviates from an initially high value of slope greater than zero to a slope of substantially zero;

generating a second signal at a time t3 when the slope increases from the slope of substantially zero to a constant slope of substantially greater than zero wherein at a time t1 the melting charge reaches the solidus temperature and at time t3 the temperature of the melting charge reaches the liquidus temperature; and generating a third signal at a time t3, for triggering the casting process, said third signal being generated when the temperature of the melting charge has been increased by a predetermined temperature increase with respect to the temperature measured when said second signal is generated.

6. Method according to claim 5, comprising:

measuring and storing actual values of the predetermined temperature increase in a first melting and casting process, and, in subsequent melting and casting processes, using one of the stored actual values as nominal values for triggering the casting process.

7. Method according to claim 6, comprising:

storing the measured variation with time of the temperature during the entire heating-up process up to the casting time in a 1st melting and casting process, and, during subsequent melting processes, comparing the variation with time of the temperature measured continuously or section by section with the stored values and, if agreement exists within predetermined tolerances between a stored and a measured variation controlling the time of casting and/or the casting temperature as a function of the casting data of the stored variation.

8. Arrangement for controlling the melting and casting process in precision casting, particularly for dental engineering, comprising:

a melting crucible for holding a melting charge;

an adjustable heating device for supplying thermal energy to the melting charge for heating thereof;

a temperature sensor for measuring the temperature of melting charge with respect to time, the system further comprising:

a control device means for triggering the casting process; calculating means for generating a slope-signal corresponding to the slope of temperature, i.e. the change with the time $(d\theta/dt)$ of the temperature of the melting charge;

1st means for generating a 1st signal at time t1 when the slope signal deviates from an initially high value greater than zero to a value of substantially zero;

second means for receiving said slope signal and for generating a second signal at a time t3 when, during supply of energy to the melting charge said slope signal increases from substantially zero to substantially greater than zero third means for receiving said second signal, wherein said third means comprises a timer which is started by said second signal for triggering the casting process at a time t'3 after a predetermined period of time has elapsed.

9. Arrangement according to claim 8, comprising a first memory for storing actual values of the predetermined period of time in a first melting and casting process and, in subsequent melting and casting processes, for using one of the stored actual values as nominal values for triggering the casting process.

10. Arrangement according to claim 9, comprising a second memory for storing the measured values of the variation with time of the temperature in a first melting and casting process, and comparison device for comparing the stored values of the variation with time with currently measured values of the variation with time of the temperature and, in case of agreement between the measured values and the stored curve variation, for outputting further values of the stored curve-variation as nominal value for the control device.

11. Arrangement for controlling the melting and casting process in precision casting, particularly for dental engineering, comprising:

a melting crucible for holding a melting charge;

an adjustable heating device for supplying thermal energy to the melting charge for heating thereof;

a temperature sensor for measuring the temperature of the melting charge with respect to time, the system further comprising:

a control device means for triggering the casting process; calculating means for generating a slope-signal corresponding to the slope of temperature, i.e. the change with the time (dθ/dt) of the temperature of the melting charge;

first means for generating a first signal at a time t1 when the slope signal deviates from an initially high value greater than zero to a value of substantially zero;

second means for receiving said slope signal and for generating a second signal at a time t3 when, during supply of energy to the melting charge said slope signal increases from substantially zero to substantially greater than zero third means for generating a reference value Δθ;

fourth means for receiving said reference value Δθ and said second signal, wherein said fourth means comprises a comparator which compares the measured temperature of the melting charge with the sum of a liquidus temperature measured at time t3 when said second signal is generated and the reference value (Δθ), said fourth means further comprising means for triggering the casting process when both compared values are equal.

12. Arrangement according to claim 11, comprising a first memory for storing the measured actual values of said predetermined value, and further comprising a reading device which, in subsequent melting and casting processes, read the stored actual values from the first memory and feeds them to the control device as nominal values for triggering the casting process.

13. Arrangement according to claim 12, comprising a third memory for storing the measured values of variation with time of the temperature and a first melting and casting process and comprising a comparison device for comparing the stored values of the variation with currently measures values of the variation with time of the temperature in subsequent melting and casting processes, and, in the case of agreement between the measured values and a stored curve variation, for outputting the further values of the stored curve variation as nominal value for the control device.

14. Arrangement according to claim 8 or 11 comprising a device for measuring the power consumed by an induction coil of said adjustable heating device and a correction device for varying the entered or stored value for triggering the casting process as a function of the output signal of the power measuring device.

* * * * *